United States Patent
Kossuth et al.

(10) Patent No.: US 9,548,215 B2
(45) Date of Patent: Jan. 17, 2017

(54) HIGH VISIBILITY ENDOPROSTHESIS AND METHOD

(71) Applicant: ABBOTT CARDIOVASCULAR SYSTEMS INC., Santa Clara, CA (US)

(72) Inventors: Mary Beth Kossuth, San Jose, CA (US); Richard J. Rapoza, San Francisco, CA (US); Joel Harrington, Redwood City, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 147 days.

(21) Appl. No.: 14/250,023

(22) Filed: Apr. 10, 2014

(65) Prior Publication Data

US 2015/0290002 A1 Oct. 15, 2015

(51) Int. Cl.
*A61F 2/89* (2013.01)
*B23K 26/00* (2014.01)
*A61F 2/95* (2013.01)
*B23K 26/40* (2014.01)
*A61B 19/00* (2006.01)
*A61B 5/00* (2006.01)
(Continued)

(52) U.S. Cl.
CPC ....... *H01L 21/31144* (2013.01); *A61B 5/0066* (2013.01); *A61B 5/0084* (2013.01); *A61B 5/4851* (2013.01); *A61B 5/6852* (2013.01); *A61L 31/146* (2013.01); *A61L 31/18* (2013.01); *H01L 21/0337* (2013.01); *A61F 2/91* (2013.01); *G01B 9/02091* (2013.01)

(58) Field of Classification Search
CPC ...... A61L 2202/24; A61L 2/081; A61L 2/087; A61L 27/34; A61L 31/06
See application file for complete search history.

(56) References Cited

U.S. PATENT DOCUMENTS

| | | | |
|---|---|---|---|
| 8,216,632 B2 * | 7/2012 | Schoenle | A61L 31/082 427/2.25 |
| 2003/0100938 A1 * | 5/2003 | Rubenchik | A61B 5/02007 623/1.1 |

(Continued)

FOREIGN PATENT DOCUMENTS

EP 842729 5/1998

OTHER PUBLICATIONS

Bezerra et al., "Intracoronary Optical Coherence Tomography: a Comprehensive Review", JACC Cardiovascular Interv. vol. 2, No. 11, pp. 1035-1046 (2009).

(Continued)

*Primary Examiner* — Baisakhi Roy
(74) *Attorney, Agent, or Firm* — Squire Patton Boggs (US) LLP

(57) ABSTRACT

An endoprosthesis, a method for imaging an endoprosthesis, a method of making an endoprosthesis involve a polymeric substrate that has been modified to have voids embedded within the substrate. The voids are sized to scatter optical radiation from within the substrate so that an optical coherence tomography (OCT) image can be obtained in which an interior region of the substrate can be easily differentiated from empty space and other structures that surround the endoprosthesis. The voids allow for OCT visualization of the polymeric substrate which may be difficult to visualize by other methods such as fluoroscopy.

15 Claims, 6 Drawing Sheets

(51) Int. Cl.
*H01L 21/311* (2006.01)
*H01L 21/033* (2006.01)
*A61L 31/14* (2006.01)
*A61L 31/18* (2006.01)
*A61F 2/91* (2013.01)
*G01B 9/02* (2006.01)

(56) References Cited

U.S. PATENT DOCUMENTS

| | | |
|---|---|---|
| 2007/0283552 A1 | 12/2007 | Gale et al. |
| 2008/0010947 A1* | 1/2008 | Huang .................... A61L 2/081 53/425 |
| 2008/0299002 A1* | 12/2008 | Freeman ................. A61L 2/087 422/22 |
| 2008/0306611 A1* | 12/2008 | Rowley .................... A61L 27/34 623/23.72 |
| 2009/0118815 A1* | 5/2009 | Arcand ................... A61L 31/08 623/1.15 |
| 2010/0256748 A1* | 10/2010 | Taylor ..................... A61L 31/10 623/1.46 |
| 2010/0305452 A1* | 12/2010 | Black ................... A61B 5/6852 600/476 |
| 2011/0057356 A1 | 3/2011 | Jow |
| 2011/0245905 A1* | 10/2011 | Weber ................... A61L 31/044 623/1.15 |
| 2011/0264190 A1* | 10/2011 | McClain ................. A61L 31/10 623/1.11 |
| 2011/0307050 A1* | 12/2011 | Harrington ............... A61F 2/91 623/1.16 |
| 2012/0323311 A1* | 12/2012 | McClain ................. A61L 31/16 623/1.42 |
| 2014/0257087 A1* | 9/2014 | Elbasiony .............. A61B 5/061 600/424 |
| 2015/0073536 A1* | 3/2015 | Rapoza ..................... A61F 2/86 623/1.38 |
| 2015/0099984 A1* | 4/2015 | Kankaria ............. A61B 5/0066 600/478 |
| 2015/0290002 A1* | 10/2015 | Kossuth ............. H01L 21/0337 623/1.16 |

OTHER PUBLICATIONS

Gutierrez-Chico et al., "Spatial Distribution and Temporal Evolution of Scattering Centers by Optical Coherence Tomography in the Poly(L-Lactide) Backbone of a Bioresorbable Vascular Scaffold", Circulation J. vol. 76, pp. 342-350 (2012).

* cited by examiner

HIGH VISIBILITY ENDOPROSTHESIS AND METHOD

FIELD OF THE INVENTION

This invention relates generally to medical imaging, endoprosthesis, and fabrication methods.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Endoluminal prostheses or endoprostheses are medical devices adapted to be implanted in a human or veterinary patient. Stents are a type of endoprosthesis which are deployed in blood vessel, urinary tract, bile duct, or other bodily lumen to provide structural support and optionally to deliver a drug or other therapeutic agent. Stents are generally cylindrical and function to hold open and sometimes expand a segment of the bodily lumen. Stents are often used in the treatment of atherosclerotic stenosis in blood vessels. Stents are often delivered to a desired location while in a reduced configuration having a smaller diameter than when fully deployed. The reduced configuration allows the stent to be navigated through very small passageways, such as coronary vessels and other bodily lumen. A crimping process is performed to place the stent in a reduced configuration. The stent can be crimped onto a catheter that can then be maneuvered over a guidewire that leads to a region of the anatomy at which it is desired to deploy the stent. The passageway through which the stent is maneuvered is often tortuous, so the stent should be capable of longitudinal flexibility. Once the stent has reached the desired deployment location, the stent is allowed to self-expand or is forcibly expanded by a balloon to an enlarged configuration. After deployment, the stent should maintain its enlarged configuration with minimal recoil back to its reduced configuration. All these functional requirements are taken into account in the structural design of a stent.

In addition to the foregoing functional requirements, it is also important for a stent to have the capability of being visualized to determine whether the stent has been properly maneuvered to the desired location and to confirm that the stent has properly deployed. Various imaging techniques, such as fluoroscopy and optical coherence tomography, may be used to obtain an image of the stent. Fluoroscopy uses X-rays while optical coherence tomography uses optical radiation.

Compared to metal stents, stents that have a polymeric substrate can be difficult to image due to their radiotranslucent and optically translucent properties. Structural features adjacent to the stent, such as parts of the anatomy and the catheter which carries the stent, can obscure the stent and make it difficult to ascertain its position. Radiopaque markers, such as metallic beads or metallic bands, can be embedded within or attached to the polymeric substrate so that the stent can be easily visualized using fluoroscopy. Radiopaque markers are relatively large in relation to the size of the stent substrate and can thereby affect stent function. Thus, stents often have only a few radiopaque markers which are strategically positioned.

Optical coherence tomography (OCT) has been used to obtain images that show individual stent struts. OCT typically employs near-infrared light which can penetrate through structures, such as biological tissue, which scatter the light. Interferometric analysis of the scattered light is used to generate images which can have a resolution in the order micrometers. International Application Publication No. WO 2010045386 A describes the use of OCT to obtain images in which reflective surfaces of metal stent struts can be identified. However, stent struts having a polymeric substrate are not as reflective as metal substrates.

OCT has been used to visualize stent struts made of a polymeric substrate. See Gutierrez-Chico et al., "Spatial Distribution and Temporal Evolution of Scattering Centers by Optical Coherence Tomography in the Poly(L-Lactide) Backbone of a Bioresorbable Vascular Scaffold" Circulation Journal, Vol. 76, 343-350 (February 2012). Gutierrez-Chico et al. describe the appearance of "scattering centers" or SC, which is defined as a "focal hyperintense backscattering signal" in the core of the stent strut. All the scattering centers were located exclusively at hinges. In a bench study, there was a complete absence of scattering centers in all regions of stents which were not subjected to crimping. After crimping and deployment, however, there were scattering centers in all hinge regions. Analysis of successive image slices through the hinges of an implanted stent showed that the scattering centers were located at the inner curvature of the hinge. Scattering centers were absent from image slices taken through the outer curvature of the hinge. As compared to the inner curvature of the hinge, parts of the stent which experienced little or no mechanical deformation during crimping and deployment appeared as "black boxes" within a dark field. The black boxes could be identified by a faint outline corresponding to the external surfaces of the stent structure.

There is a need for an imaging method, stent manufacturing method, and stent which allow for improved OCT imaging that can make it easier to determine where the stent structure begins or ends within a bodily lumen and make it easier to evaluate whether the stent has been properly deployed and is supporting surrounding tissue.

SUMMARY

Described herein are an endoprosthesis, a method of imaging an endoprosthesis, and a method of making an endoprosthesis.

Various aspects of the invention are directed to a method for imaging an endoprosthesis having a substrate that has been modified by a laser to have voids embedded within the substrate. The voids are sized to increase scattering of optical radiation from within the substrate. The method comprises passing optical radiation across an external surface of the substrate of the endoprosthesis, and obtaining an image by optical coherence tomography (OCT) processing of light that has been scattered by the voids from within the substrate. The obtained image includes an image signal corresponds to an interior substrate portion having the voids. The image signal differentiates the interior substrate portion having the voids from empty space outside of the substrate.

Various aspects of the invention are directed to a method of making an endoprosthesis. The method comprises modifying a substrate of an endoprosthesis with a laser to form voids embedded within the substrate. The voids are sized to scatter optical radiation from within the substrate so as to produce an optical coherence tomography (OCT) image that distinguishes an interior region of the substrate from empty space outside of the substrate.

Various aspects of the invention are directed to an endoprosthesis comprises a plurality of radially deformable rings. Each ring comprises a polymeric substrate, and a plurality of voids is embedded within at least a portion of the substrate. The voids are sized to scatter optical radiation that has passed across an external surface of the substrate to produce an optical coherence tomography (OCT) image that distinguishes an interior region of the substrate from empty space outside of the substrate.

The features and advantages of the invention will be more readily understood from the following detailed description which should be read in conjunction with the accompanying drawings.

DETAILED DESCRIPTION OF EXEMPLARY EMBODIMENTS

As used herein, an endoprosthesis is a device that can be implanted in a human or veterinary patient. Examples of such devices include without limitation self-expandable stents, balloon-expandable stents, stent-grafts, grafts (e.g., aortic grafts), heart valve prosthesis (e.g., artificial heart valves), vascular graft, and shunts.

Figure 1:
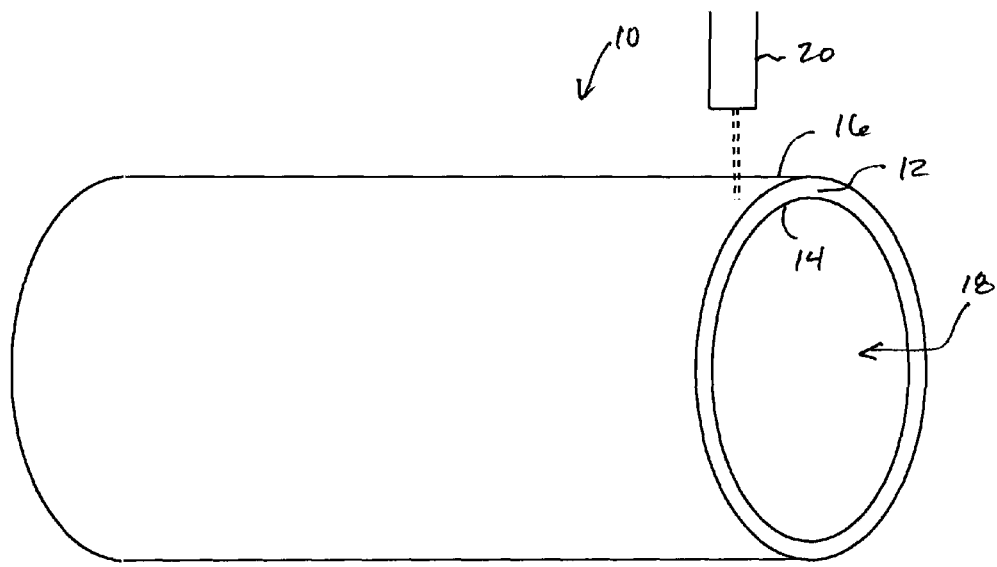
FIG. 1 is a perspective view showing an endoprosthesis being modified to increase its ability to reflect and scatter light from within the substrate of the endoprosthesis.

Referring now in more detail to the exemplary drawings for purposes of illustrating embodiments of the invention, wherein like reference numerals designate corresponding or like elements among the several views, there is shown in FIG. 1 endoprosthesis 10 in the form of a tube without fenestrations. The tube can be made by extruding or molding polymeric material, or the tube can be made by rolling a sheet of polymeric material. The tube has polymeric substrate 12. The term "substrate" refers to the structural support material. After endoprosthesis 10 is implanted in a patient, the strength of substrate 12 allows the endoprosthesis to provide support to surrounding tissue or perform any other intended function. Optionally, substrate 12 may be covered by a relatively thin coating from which a drug or other therapeutic agent may be released into a patient.

As will be discussed in more detail below, when an optical coherence tomography (OCT) technique is used, optical radiation is emitted toward polymeric substrate 12. External surfaces of the endoprosthesis scatter the light due to a change in the index of refraction between the external surface and a fluid (i.e., air or liquid) adjacent to the external surface. External surfaces include luminal surface 14 and abluminal surface 16. The term "luminal surface" refers to the radially inward facing surface or the surface that faces toward central passageway or lumen 18 of endoprosthesis 10. The term "abluminal surface" refers to the radially outward facing surface or the surface that faces away from central lumen 18. The light scattered from external surfaces can provide an OCT image that shows an outline of the external surfaces. As used herein, the term "OCT image" is an image that is produced using an OCT technique.

Laser modifying device 20 is used to modify substrate 12 to increase its ability to reflect and scatter light from within substrate 12. The modification creates changes in the index of refraction within substrate 12. After the modification, optical radiation from an OCT technique will penetrate through the external surfaces and then be reflected and scattered from within the substrate, such that an OCT image can show an image signal from inside the substrate that would normally not be present.

Figure 2:
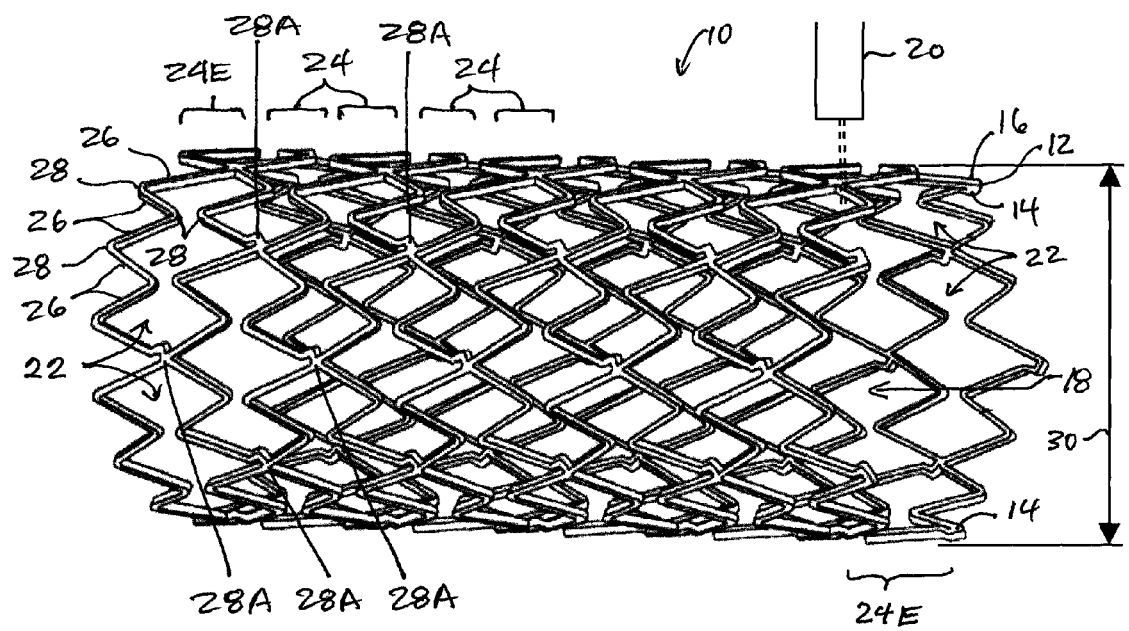
FIG. 2 is a perspective view showing another endoprosthesis being modified to increase its ability to reflect and scatter light from within the substrate.

As shown in FIG. 2, endoprosthesis 10 can be a stent in the form of tubular scaffold. The tubular scaffold is a tube with fenestrations 22. The term "fenestrations" refers to holes or gaps through the wall of the tube. Endoprosthesis 10 includes a plurality of radially deformable rings 24. Each ring 24 comprising a series of ring struts 26. Each ring strut 26 is connected by hinge 28 to adjacent ring strut 26. Ring struts 26 and hinges 28 are constructed of polymeric substrate 12. The strength and elasticity of substrate 12 allows endoprosthesis 10 to be crimped to a reduced configuration, deployed to an enlarged configuration, and then provide support to surrounding tissue. Each ring 24 is connected by hinges 28 (further identified with the letter "A") to adjacent ring 24. All hinges 28 are configured to bend during crimping and deployment of endoprosthesis 10. During crimping and deployment, hinges 28 mechanically deform to allow a change in overall outer diameter 30 of each ring 24. End rings 24 (further identified with the letter "E") are located at opposite ends of endoprosthesis 10.

Fenestrations 22, ring struts 26, and hinges 28 can be formed during an injection molding process using a mold having a cavity with a shape that corresponds to the shape of the fenestrations, ring struts, and hinges. Molten polymeric material can be injected into the mold to form the scaffold of FIG. 2. After the polymeric material has been cooled and hardened, the tube can be removed from the mold and then laser modifying device 20 can be used to modify substrate 12.

Alternatively, fenestrations 22, ring struts 26, and hinges 28 can be formed by cutting away material from a tube of polymeric material. Optionally, the tube of polymeric material can be made by extruding a polymer through a die to form a precursor tube. The precursor tube can be radially expanded by a blow molding process to induce polymer molecule chains to have a preferential orientation that provides desirable structural characteristics. Blow molding can be performed as described in U.S. Publication No. 2011/0066222 A1. After blow molding, material is cut away from the radially expanded tube to form the scaffold of FIG. 2. Cutting can be performed as described in U.S. Publication No. 2007/0283552 A1. Cutting can be performed using a mechanical knife, a cutting laser device, or other device. After material is cut away from the radially expanded tube to form ring struts 26 and hinges 28, laser modifying device 20 can be used to modify substrate 12 to increase the ability of the substrate to reflect and scatter light from within the substrate. In further embodiments, the modification process using laser modifying device 20 can be performed at a time between completion of blow molding and the start of cutting.

In another alternative, fenestrations 22, ring struts 26, and hinges 28 can be formed by cutting away material from a flat sheet of polymeric substrate material, which is then rolled to form the scaffold of FIG. 2. Cutting can be performed using a mechanical knife, a cutting laser device, or other device. After material is cut away from the flat sheet, laser modifying device 20 can be used to modify substrate 12 to increase the ability of the substrate to reflect and scatter light from within the substrate. Alternatively, the modification process using laser modifying device 20 can be performed before material is cut away.

As mentioned above, a cutting laser device can be used to cut away material to form fenestrations 22, ring struts 26, and hinges 28. The cutting laser device is adjusted to cut entirely through the wall thickness of the tube. The cutting laser device can be a femtosecond laser modifying device which is controlled in terms of power, pulse duration, pulse repetition rate, wavelength, focus, and other laser device variables in order to remove material and cut completely through the substrate material. As discussed in U.S. Publication No. 2011/0307050 A1, the laser device variables can be set such that there is minimal disruption to the substrate material below the surface being cut.

Laser modifying device 20 can be a femtosecond laser modifying device, which can be the same laser device which was used to cut away material or a different laser device. In order to modify the interior of substrate 12 to increase light reflection and scattering from within the substrate, laser modifying device 20 is controlled in terms of power, pulse duration, pulse repetition rate, wavelength, focus, and other variables so as not to cut entirely through the substrate material. Settings for the laser device variables used to modify the interior of substrate 12 are different than settings used to cut entirely through the substrate material to produce fenestrations 22, ring struts 26 and hinges 28. To modify the interior of substrate 12, the laser device variables are controlled to produce tiny gas-filled voids below the surface of substrate 12. The laser modifying device can focus one or more laser beams onto a region below an external surface of substrate 12 to induce a nonthermal and photochemical process that breaks chemical bonds in the region below the external surface, which results in the gas-filled voids. Due to translucency of the substrate material, the external surface above the gas-filled voids can remain in place and undamaged. In some instances, the external surface above the gas-filled voids can remain in place with some alteration but still cover over the gas-filled voids. During the modification process, cool air may be blown onto the external surface to prevent or minimize disruption of the external surface.

The gas-filled voids can have a diameter or interior dimension that is greater than 1 µm, greater than 2 µm, or greater than 3 µm. Although the term "diameter" is used to describe the size of the gas-filled voids, it should be understood that the gas-filled voids can be irregularly shaped, ellipsoid in shape, or spherical in shape. The gas-filled voids can have any enclosed shape. The term "enclosed shape" means that the void does not open to an external surface of substrate 12. Voids having the aforementioned diameters can be located at a depth below the external surface nearest the void, the depth being more than 2 µm, more than 10 µm, or more than 30 µm. Each void within substrate 12 provides an interface between gas and polymer, which is also referred to as a gas-polymer interface. The gas-polymer interface corresponds to a change in the index of refraction between gas and polymer, which causes light radiation passing through the external surface to scatter upon reaching the voids. In an OCT technique, the scattered light is processed to produce an OCT image having an increase in image signal intensity from within substrate 12 as compared to a region of the substrate that does not have gas-filled voids.

FIG. 2 shows endoprosthesis 10 before it has been crimped to a reduced configuration. After laser modifying device 20 is used to modify substrate 12, endoprosthesis 10 can be crimped onto a catheter so that endoprosthesis 10 has a reduced configuration, and then deployed to an enlarged configuration within a blood vessel or other bodily lumen.

Alternatively, laser modifying device 20 can be used to modify substrate 12 after it has been crimped onto a catheter. The laser beam can be carefully controlled, such as by use of a feedback camera, to avoid the catheter beneath the substrate. After the substrate 12 is modified to have gas-filled voids, endoprosthesis 10 can be deployed within a blood vessel or other bodily lumen.

Figure 3:
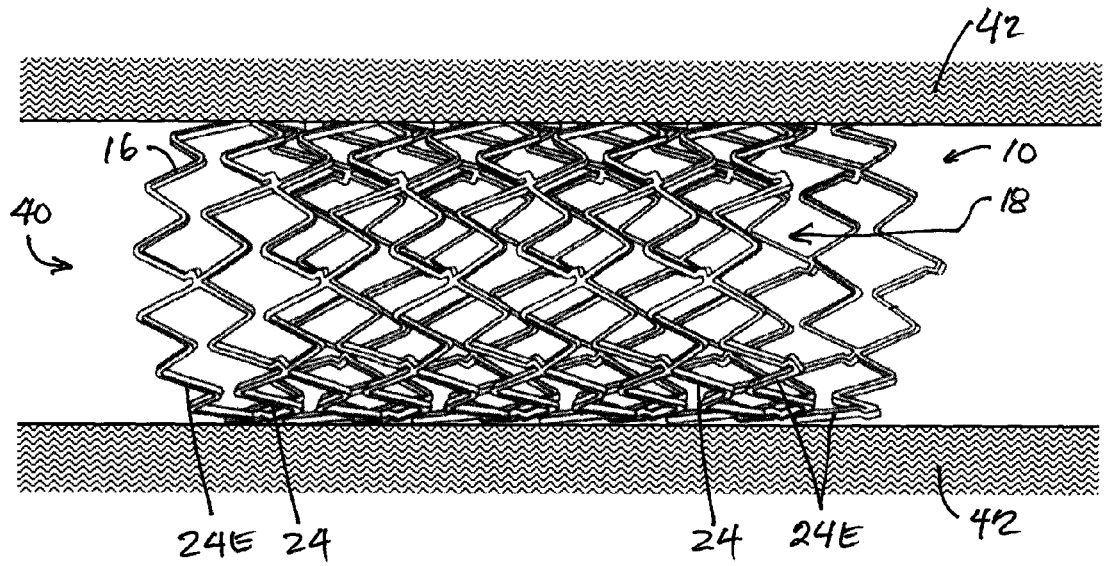
FIG. 3 is a perspective view showing the endoprosthesis of FIG. 2 after being deployed in a lumen.

FIG. 3 shows endoprosthesis 10 after substrate 12 has been modified using laser modifying device 20 and after endoprosthesis 10 has been deployed with lumen 40. For example, after the interior of substrate 12 has been modified to have gas-filled voids, a catheter can be used to maneuver endoprosthesis 10 to a desired location while endoprosthesis 10 is in a reduced configuration. When at the desired location, endoprosthesis 10 is allowed to expand or is forcibly expanded to an enlarged configuration. Abluminal surfaces 16 of endoprosthesis 10 provide support to lumen walls 42 which are shown in cross-section. Lumen walls 42 can be, for example, the walls of a blood vessel or other bodily lumen.

Figure 4:
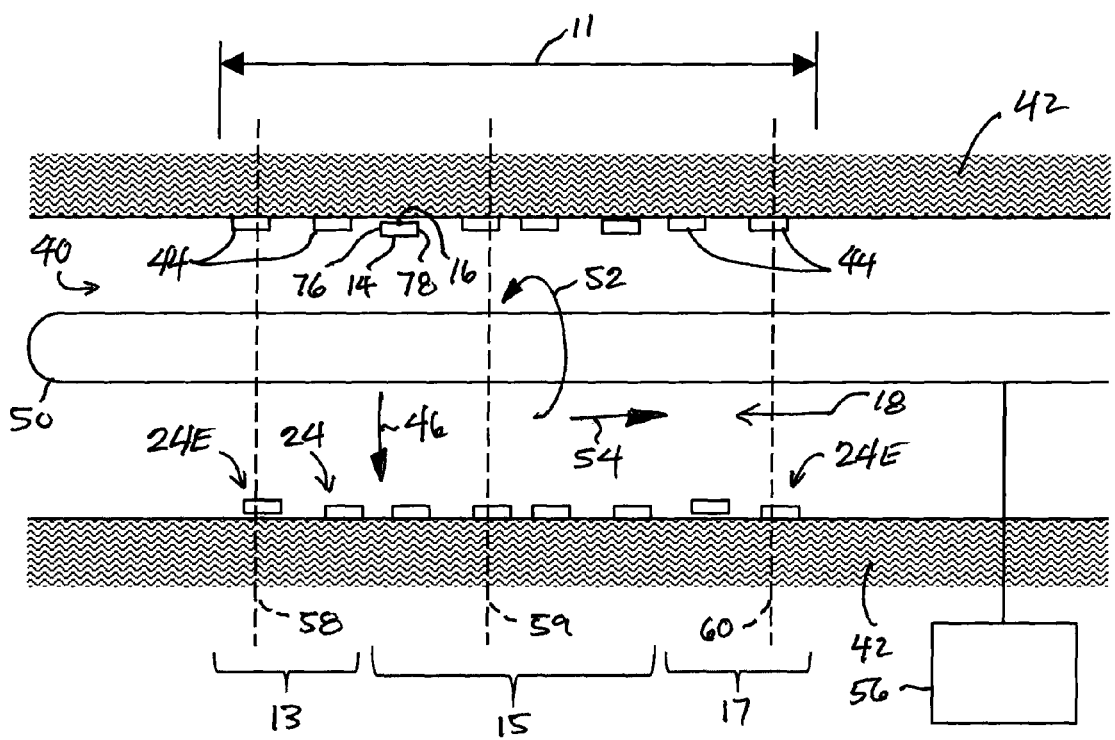
FIG. 4 is a cross-section view showing the endoprosthesis of FIG. 3 while deployed in the lumen.

FIG. 4 shows a length-wise slice of endoprosthesis 10 of FIG. 3. Polymeric substrate 12 of endoprosthesis 10 was modified to have gas-filled voids before endoprosthesis 10 was deployed in lumen 40. The slice shows the entire longitudinal length 11 of endoprosthesis 10. The small rectangles 44 are schematic representations of ring struts 26 and hinges 28 intersected by the slice. Catheter 50 is inserted through central lumen 18 of endoprosthesis 10. Catheter 50 has a fiber optic wire that is configured to emit light radially outward, such as in the direction of arrow 46, toward endoprosthesis portions 44. The light passes through the external surfaces of endoprosthesis portions 44 and lumen wall 42 and is reflected and scattered from within endoprosthesis portions 44 and lumen wall 42. The fiber optic wire of catheter 50 is configured to sense the light scattered by endoprosthesis portions 44 and lumen wall 42. While emitting light and sensing scattered light, catheter 50 can be rotated about its axis, such as in the direction of arrow 52, and simultaneously pulled axially, such as in the direction of arrow 54. Rotation and pulling allow light to be scattered and then sensed from the entire longitudinal length 11 of endoprosthesis 10 and from the entire circumference of each ring 24.

Catheter 50 is coupled to a processor, which is schematically represented by box 56. Processor 56 is configured to apply interferometric processing to the scattered light sensed by catheter 50 to generate image data representative of endoprosthesis 10 and lumen wall 42 that surrounds endoprosthesis 10. The image data can be used to generate a plurality of images, each image being a circumferential slice taken at a different position along longitudinal length 11 of endoprosthesis 10. For example, one of the images can be that of a circumferential slice at plane 59 to show a stent ring at middle segment 15 of endoprosthesis 10. Other images can be that of circumferential slices at planes 58 and 60 to show end rings 24E at opposite end segments of endoprosthesis 10. The opposite end segments are distal end segment 13 and proximal end segment 17 of endoprosthesis 10. The image data can also be used to generate a three-dimensional image of endoprosthesis 10.

Catheter 50 and processor 56 can be configured for OCT imaging. In which case, catheter 50 can be configured to emit infrared light that passes through the external surfaces of endoprosthesis portions 44 and lumen wall 42. As used herein, the term "infrared light" encompasses any wavelength from a nominal red edge of the visible spectrum at 700 nanometers (nm) to 1 mm. The infrared light can be short wavelength infrared (1.4 to 3 μm wavelength), near-infrared light (0.75 to 1.4 μm wavelength), mid-infrared light (6 to 8 μm wavelength), or other infrared wavelengths. Selection of wavelength can depend on the specific polymeric substrate material of endoprosthesis 10 and the desired depth through tissue at which an image is to be taken.

Catheter 50 can be configured to sense the near-infrared light (or other light wavelength mentioned above) that was scattered from within endoprosthesis portions 44 and lumen wall 42. Processor 56 can be configured to apply OCT processing techniques to the scattered light sensed by catheter 50 to generate image data representative of endoprosthesis 10 and lumen wall 42. Image data for the entire longitudinal length of the endoprosthesis can be obtained by rotating and pulling catheter 50 as previously described.

Figure 5:
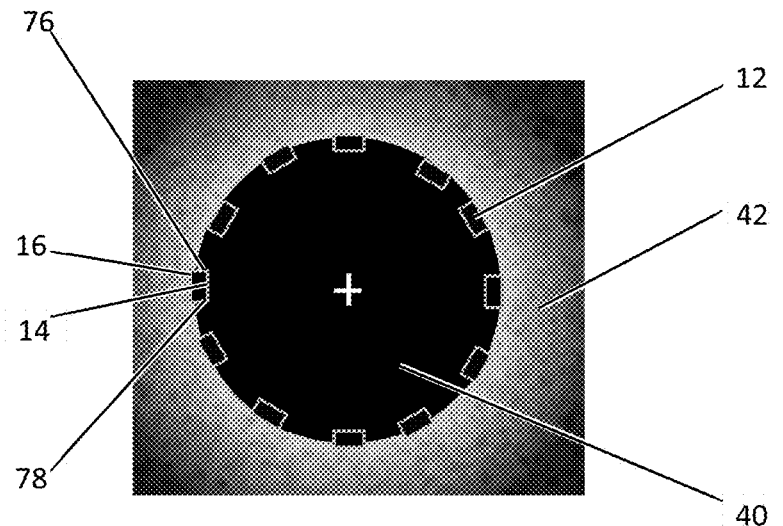
FIGS. 5 and 6 are simulated optical coherence tomography (OCT) images of a stent, such as the endoprosthesis in FIG. 4.

FIG. 5 shows a simulated OCT image showing a circumferential slice of one or more stent rings 24 of endoprosthesis 10 of FIGS. 3 and 4 deployed in lumen 40. Image signals, which appear light in color in FIG. 5, represent regions from which light was scattered after the light was emitted from a central region of lumen 40 represented generally by a "+" mark. The substrate material of the stent ring has not been modified to increase the ability of the substrate to reflect and scatter light from within the substrate. Thus, portions of substrate 12 intersected by the slice have image signals (appearing as a light color rectangle) that identify the external surfaces of substrate 12. The absence of an image signal from within substrate 12 causes the area within the substrate to appear dark in the OCT image. The color of the interior region within substrate 12 is that same as that of the empty space at the center of lumen 40. Structures within lumen wall 42 surrounding the endoprosthesis scatter light and thus provide a ring-shaped image in which the strength of the image signal fades or becomes weaker with increasing distance from the OCT light source near the "+" mark.

Figure 6:
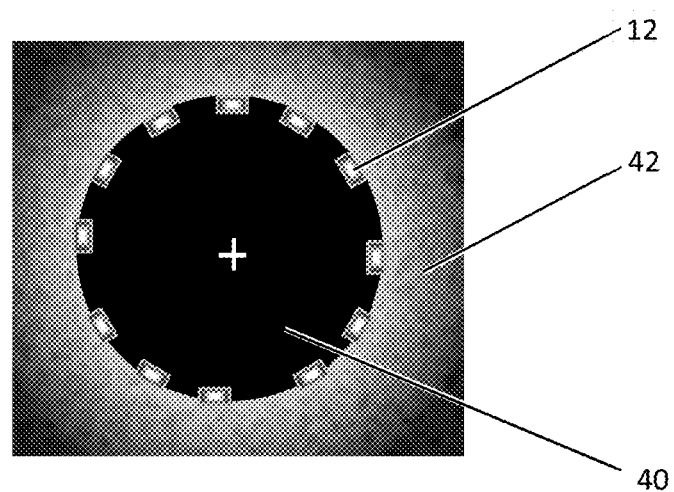

FIG. 6 shows a simulated OCT image showing a circumferential slice of one or more stent rings 24 of endoprosthesis 10 of FIGS. 3 and 4. The OCT image is similar to that of FIG. 5 except substrate 12 has been modified to increase the ability of the substrate to reflect and scatter light from within the substrate. Thus, portions of substrate 12 in the slice have image signals (appearing as a light color rectangle) that identify the external surfaces of substrate 12, and they also have image signals within substrate 12 that causes the area within the substrate to appear bright. The image signal intensity from the interior of substrate 12 in FIG. 6 is greater than that in FIG. 5. Also, the region within substrate 12 is much brighter than the empty space at the center of lumen 40. In FIG. 6, the increase in brightness from within substrate 12 can help distinguish endoprosthesis structures from the empty space and from surrounding lumen walls 42.

In some embodiments, middle segment 15 of endoprosthesis 10 has not been modified by laser modifying device 20 in the manner described above. Substrate 12 in the middle segment does not have gas-filled voids that increase the ability of the substrate to reflect and scatter light from within the substrate. End segments 13 and 17 of endoprosthesis 10 have been modified by laser modifying device 20 to have gas-filled voids that increase the ability of the substrate to reflect and scatter light from within the substrate. In these embodiments, the simulated OCT image of FIG. 5 may represent a circumferential slice taken through plane 59 in FIG. 4, and the simulated OCT image of FIG. 6 may represent circumferential slices taken through planes 58 and 60 in FIG. 4.

In other embodiments, end segments 13 and 17 of endoprosthesis 10 have not been modified by laser modifying device 20 in the manner described above. Substrate 12 in end segments 13 and 17 do not have gas-filled voids that increase the ability of the substrate to reflect and scatter light from within the substrate. Middle segment 15 of endoprosthesis 10 has been modified by laser modifying device 20 to have gas-filled voids that increase the ability of the substrate to reflect and scatter light from within the substrate. In these embodiments, the simulated OCT image of FIG. 5 may represent circumferential slices taken through planes 58 and 60 in FIG. 4, and the simulated OCT image of FIG. 6 may represent a circumferential slice taken through plane 59 in FIG. 4. It is possible to modify substrate 12 in end rings 24E exclusively to help determine where the endoprosthesis structure begins and ends when implanted in lumen 40.

In yet other embodiments, substrate 12 throughout longitudinal length 11 of endoprosthesis 10 has been modified by laser modifying device 20 to have gas-filled voids that increase the ability of the substrate to reflect and scatter light from within the substrate. In these embodiments, the simulated OCT image of FIG. 6 may represent circumferential slices taken through planes 58, 59, and 60 in FIG. 4 and anywhere else along longitudinal length 11 of endoprosthesis 10.

As discussed above, substrate 12 can be modified to have gas-filled voids in order to distinguish some longitudinal segments (e.g., end segments) from other longitudinal segments (e.g., a middle segment). Also, substrate 12 of one or more rings 24 can be modified to have gas-filled voids in ring struts 26 but not modified to have gas-filled voids in hinges 28 so as not to affect the elasticity and strength of the hinges. Further, substrate 12 throughout longitudinal length 11 of endoprosthesis 10, except hinges 28, can be modified by laser modifying device 20 to have gas-filled voids that increase the ability of the substrate to reflect and scatter light from within the substrate. As discussed below, substrate 12 can also be modified to distinguish a surface of the endoprosthesis (e.g., abluminal surface) from another surface of the endoprosthesis (e.g. luminal surface).

Figure 7:
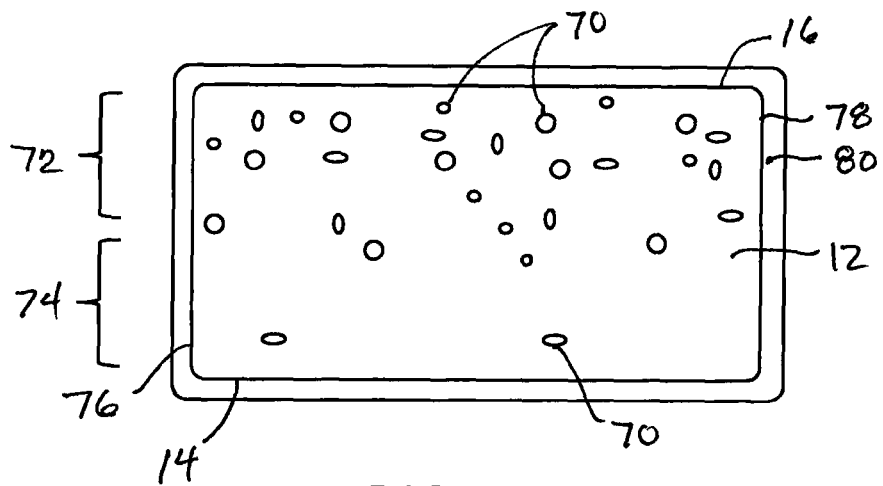
FIGS. 7-9 are cross-section showing a substrate after being modified to have voids that increase light scattering from within the substrate.

FIG. 7 shows a cross-section of a portion of substrate 12 which has been modified by laser modifying device 20 to have gas-filled voids 70 that increase the ability of the substrate to reflect and scatter light from within the substrate. Gas-filled voids 70 have a non-uniform spatial density as viewed in the illustrated cross-section of substrate 12. As used herein, "spatial density" refers to the total number of voids per unit area. For example, spatial density can be measured in terms of the total number of voids per 1000

μm². The spatial density decreases with increasing distance from abluminal surface 16. The spatial density is greater in area 72 adjacent to abluminal surface 16 of the endoprosthesis as compared to area 74 adjacent to luminal surface 14. Areas 72 and 74 are interior substrate portions. The greater spatial density in area 72 corresponds to a greater number of gas-polymer interfaces in area 72, which results in a greater scattering of light and thus a greater OCT image signal that could enhance visualization of abluminal surface 16.

Figure 8:
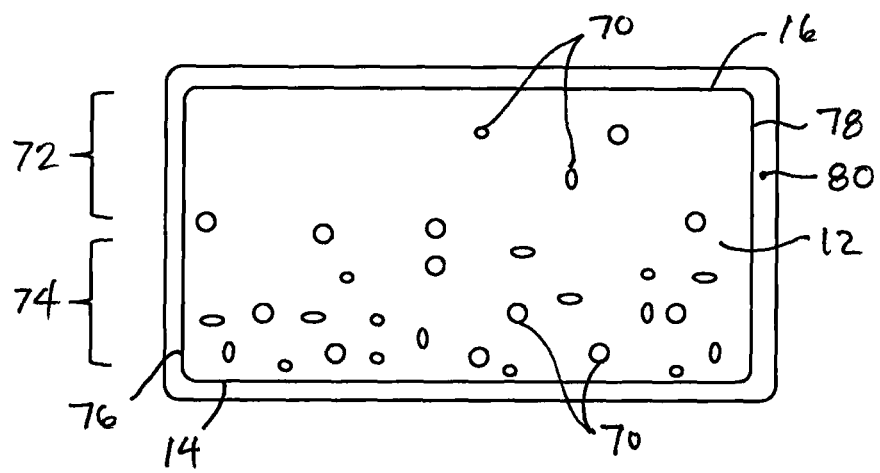

FIG. 8 shows a cross-section of a portion of substrate 12 which has been modified by laser modifying device 20 to have gas-filled voids 70 that increase the ability of the substrate to reflect and scatter light from within the substrate. The spatial density increases with increasing distance from abluminal surface 16. The spatial density of gas-filled voids 70 is greater in area 74 as compared to area 72. The greater spatial density in area 74 could enhance visualization of luminal surface 14.

A greater spatial density can be created in a preferred area (either area 72 or 74) by controlling laser modifying device 20 to create more gas-filled voids in the preferred area. For example, laser modifying device 20 can be configured to focus energy in the preferred area instead of another area of substrate 12. Also, laser modifying device 20 can be arranged to emit a laser beam that enters substrate 12 from one of the external surfaces (abluminal surface 16 or luminal surface 14) that is closest to the preferred area.

Figure 9:
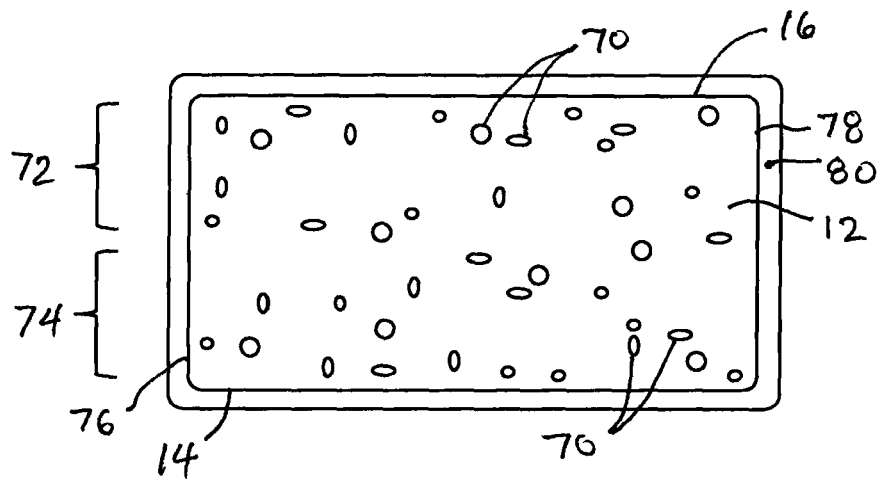

FIG. 9 shows a cross-section of a portion of substrate 12 which has been modified by laser modifying device 20 to have gas-filled voids 70 that increase the ability of the substrate to reflect and scatter light from within the substrate. The spatial density of gas-filled voids 70 in area 72 is about the same as that in area 74 so that there is a substantially uniform spatial density. The terms "about the same" and "substantially uniform" mean that the number of gas-filled voids in area 72 can be within plus or minus 20% of the number of gas-filled voids in area 74. The substantially uniform spatial density can be created by controlling laser modifying device 20 to create about the same number of gas-filled voids in areas 72 and 74. For example, laser modifying device 20 can be configured to focus about the same amount of energy in areas 72 and 74. Also, laser modifying device 20 can be arranged to emit a laser beam that enters substrate 12 from one of the external surfaces (abluminal surface 16 or luminal surface 14) and then, at a later time, emit a laser beam that enters substrate 12 from the opposite external surface.

Figure 11:
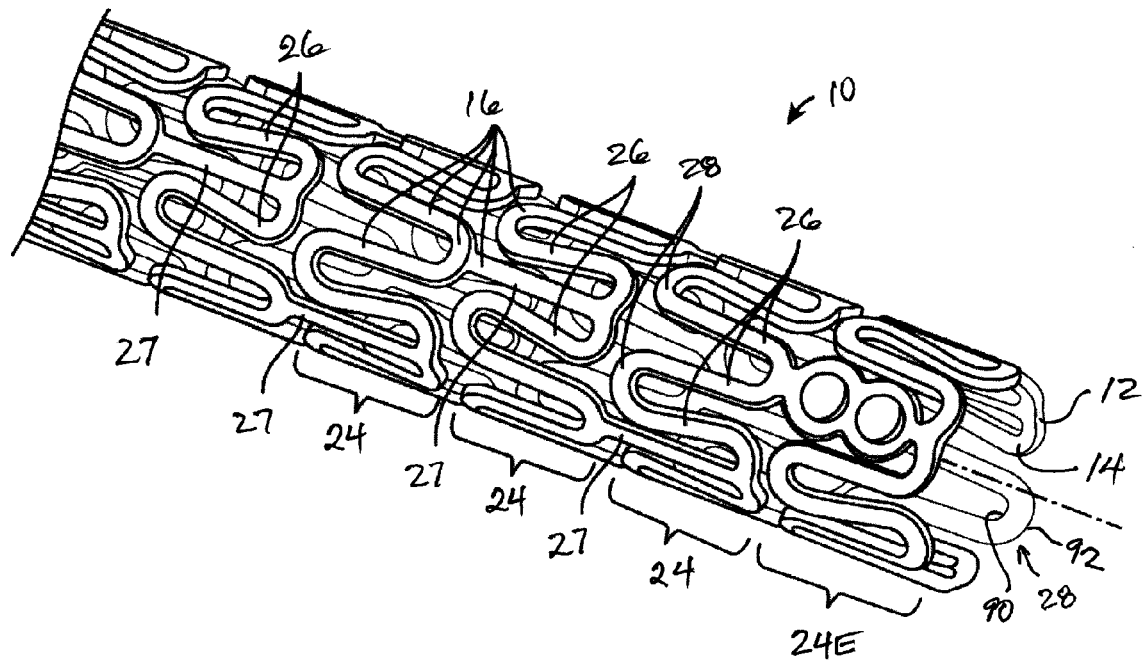
FIG. 11 is a perspective view showing an endoprosthesis that can be modified to increase its ability to reflect and scatter light from within the substrate.
Figure 12A:
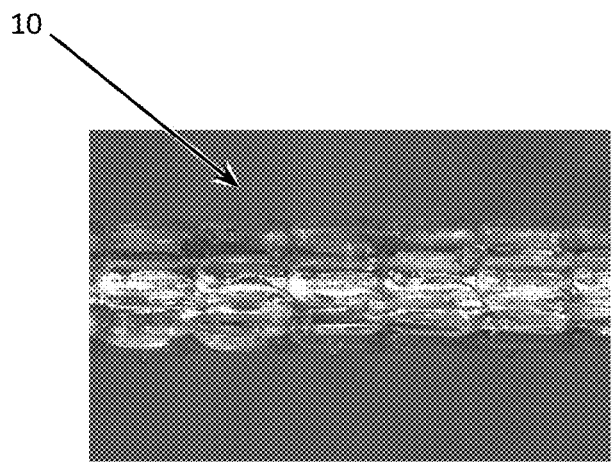
FIGS. 12A and 12B are photographs showing an endoprosthesis, in crimped and deployed states, that can be modified to increase its ability to reflect and scatter light from within the substrate.
Figure 12B:
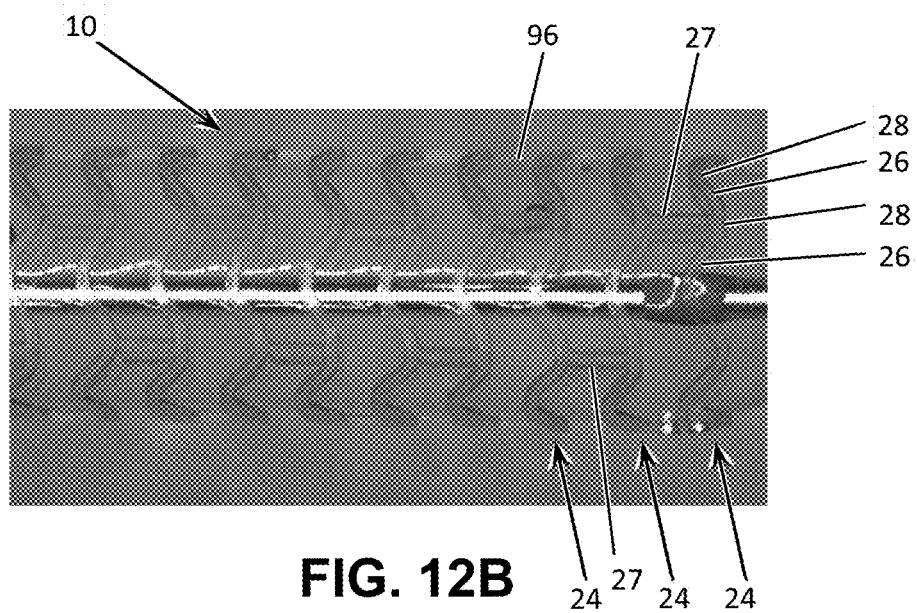

In FIGS. 7-9, the illustrated cross-sections of substrate 12 can be that of ring strut 26, hinge 28 or any other part of endoprosthesis 10, such as link strut 27 of FIGS. 11 and 12B. The illustrated cross-section can be a longitudinal cross section, similar in orientation to the substrate cross-sections shown in FIG. 4. The illustrated cross-section can be circumferential cross sections, similar in orientation to the substrate cross-sections shown in FIG. 6.

The cross-sections of FIGS. 7-9 show luminal surface 14 and abluminal surface 16 which face in opposite directions. Side surfaces 76 and 78 connect luminal surface 14 to abluminal surface 16. Gas filled voids 70 are encapsulated within substrate 12. Gas filled voids 70 are sealed within luminal surface 14, abluminal surface 16, and side surfaces 76 and 78. Gas filled voids 70 are not necessarily illustrated to scale. Gas-filled voids 70 can have a diameter or interior dimension that is greater than 1 μm, greater than 2 μm, or greater than 3 μm. Gas-filled voids 70 can be located at a depth beyond the external surface nearest the void, the depth being greater than 2 μm, greater than 10 μm, greater than 30 μm, greater than 50 μm, or not greater than 50 μm. For example, gas-filled voids 70 can be located at depths greater than 2 μm, greater than 10 μm, greater than 30 μm, or greater than 50 μm from any one or more of luminal surface 14, abluminal surface 16, side surface 76, and side surface 78. As further example, there can be gas-filled voids at depths up to 50 μm but not greater than 50 μm as measured from any one of luminal surface 14, abluminal surface 16, side surface 76, and side surface 78.

Side surfaces 76 and 78 can be formed by a laser cutting device which cuts entirely through a sheet or tube of polymeric substrate material to form fenestrations 22, ring struts 26, hinges 28, and other parts of endoprosthesis 10. In some embodiments, area 72 is an area of substrate 12 adjacent to abluminal surface 16 and which extends from one side surface 76 to the opposite side surface 78. Area 74 is an area of substrate 12 adjacent to luminal surface 14 and which extends from one side surface 76 to the opposite side surface 78. The distance from side surface 76 to opposite side surface 78 is referred to as the width of the cross-section.

Optionally, coating 80 can be applied on an external surface of substrate 12, such as by spraying, dipping, or other method. Gas-filled voids 70 are sealed within coating 80. Coating 80 may include a polymeric coating material. Coating 80 may also include a drug or other type of therapeutic agent carried by the polymeric coating material. Substrate 12 may be modified to have gas-filled voids before or after coating 80 is applied on substrate 12. To avoid damage to substances in coating 80, substrate 12 is preferably modified by laser modifying device 20 to have gas-filled voids before coating 80 is applied on substrate 12.

Figure 10:
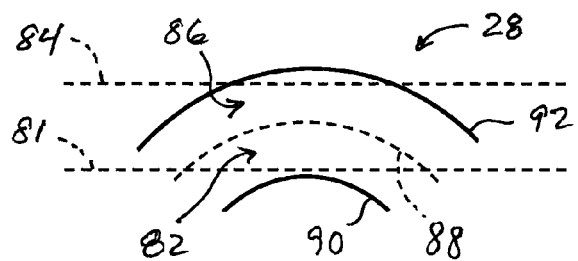
FIG. 10 is a plan view showing a hinge of an endoprosthesis through which the cross-sections of FIGS. 7-9 may be taken.

Referring to FIG. 10, the illustrated cross-sections of FIGS. 7-9 can be a slice through plane 81 at inner curvature 82 of hinge 28. The illustrated cross-sections of FIGS. 7-9 can be a slice through plane 84 at outer curvature 86 of hinge 28. Geometric central axis 88 separates inner curvature 82 from outer curvature 86. Geometric central axis 88 is centered between side surfaces 90 and 92.

It is to be understood that that the structural pattern for endoprosthesis 10 is not necessarily limited to what is depicted in FIGS. 2 and 3. The structural pattern refers to the arrangement, and orientation of rings and of the various struts, hinges, and other structural elements. The structural pattern can be any of the stent patterns described in U.S. Pat. Nos. 7,476,245 and 8,002,817. The stent can have virtually any stent pattern suitable for a polymer substrate.

Referring to FIG. 11, endoprosthesis 10 can have a strut pattern having radially deformable rings 24 connected to each other by link struts 27. Opposite ends of link struts 27 meet hinges 28 of adjacent rings 24. Substrate 12 of link struts 27 can be modified to have gas-filled voids 70 in the manner described above in FIGS. 7-9 and in the same manner described above for any part of the endoprosthesis of FIGS. 3 and 4.

FIGS. 12A and 12B show photographs of endoprosthesis 10 having radially deformable rings 24 which are interconnected by link struts 27 similar to the scaffold shown in FIG. 11. Substrate 12 of endoprosthesis 10 is made of poly(L-lactic acid) which was extruded to form a precursor tube, then radially expanded by blow molding, and then cut using a laser cutting device to form the scaffold. In FIG. 12A, the scaffold has been crimped to a reduced configuration on a balloon catheter. In FIG. 12B, the scaffold has been forcibly expanded to an enlarged configuration in which the inner diameter of each ring 24 is 3.5 mm. Expansion is accomplished by inflation of balloon 96 of the catheter. Compared to ring struts 26 and link struts 27, it is the hinges 28 that perform most of the bending and flexing needed to allow the diameter of endoprosthesis 10 to be reduced during crimping and enlarged during subsequent expansion. As can be seen in FIGS. 12A and 12B, ring struts 26 and link struts 27 remain substantially straight during crimping and expansion. Substrate 12 can be modified to have gas-filled voids before or after being crimped on a catheter. During the modification process, the optical translucency of substrate 12 allows energy from laser modifying device 20 to pass across the external surface of the substrate and induce a process that breaks chemical bonds in the region below the external surface, which results in the gas-filled voids within the substrate. Substrate 12 of endoprosthesis 10 can be modified to have gas-filled voids in ring struts 26, link struts 27, and hinges 28. Alternatively, substrate 12 of endoprosthesis 10 can be modified to have gas-filled voids in ring struts 26 and link struts 27 but not modified to have gas-filled voids in hinges 28 so as not to affect the elasticity and strength of the hinges. During an OCT imaging process, the optical translucency of the substrate allows light directed toward the substrate to pass across the external surface of the substrate and be scattered by gas-filled voids. Scattering of light from within the substrate increases the image signal of the endoprosthesis structure.

In any of the above embodiments, substrate 12 is made of a material that is not metal. In any of the above embodiments, substrate 12 is made of a polymeric substrate material that can be penetrated by near-infrared light (or other light wavelength mentioned above) used in an OCT technique. The polymeric substrate material can be bioresorbable.

As used herein, the terms "biodegradable," "bioabsorbable," "bioresorbable," and "bioerodable" are used interchangeably and refer to materials that are capable of being completely degraded, eroded, and/or dissolved when exposed to bodily fluids such as blood and can be gradually resorbed, absorbed, and/or eliminated by the body. The processes of breaking down and absorption of the polymer can be caused by, for example, hydrolysis and metabolic processes.

The polymeric substrate material can be poly(lactic acid) or a polymer based on poly(lactic acid). Polymers based on poly(lactic acid) include graft copolymers, block copolymers, such as AB block-copolymers ("diblock-copolymers") or ABA block-copolymers ("triblock-copolymers"), and mixtures thereof. Examples of polymeric substrate materials include without limitation poly(lactide-co-glycolide), poly(glycolic acid), poly(glycolide), poly(L-lactic acid), poly(L-lactide) (PLLA), poly(D,L-lactic acid), and poly(caprolactone) (PCL) copolymers. As a further example, substrate 12 can be made from a PLLA/PCL copolymer.

The coating that is optionally applied on substrate 12 can include a polymer, examples of which include without limitation ethylene vinyl alcohol copolymer (commonly known by the generic name EVOH or by the trade name EVAL), poly(butyl methacrylate), poly(vinylidene fluoride-co-hexafluororpropene) (e.g., SOLEF 21508, available from Solvay Solexis PVDF, Thorofare, N.J.), polyvinylidene fluoride (otherwise known as KYNAR, available from ATO-FINA Chemicals, Philadelphia, Pa.), ethylene-vinyl acetate copolymers, and polyethylene glycol.

The coating that is optionally applied on substrate 12 can include a drug or other therapeutic agent, examples of which include without limitation sirolimus (rapamycin), everolimus, zotarolimus, Biolimus A9, AP23572, tacrolimus, pimecrolimus and derivates or analogs or combinations thereof. The therapeutic agent can be an antiproliferative, antineoplastic, anti-inflammatory, antiplatelet, anticoagulant, antifibrin, antithrombin, antimitotic, antibiotic, antiallergic, or antioxidant substance.

The methods described above for modifying substrate 12 to have gas-filled voids to facilitate OCT imaging can be applied to a polymeric substrate in various implantable medical devices, such as pacemaker electrodes, and catheters.

While several particular forms of the invention have been illustrated and described, it will also be apparent that various modifications can be made without departing from the scope of the invention. It is also contemplated that various combinations or subcombinations of the specific features and aspects of the disclosed embodiments can be combined with or substituted for one another in order to form varying modes of the invention. Accordingly, it is not intended that the invention be limited, except as by the appended claims.

What is claimed is:

1. A method for imaging a radially expandable endoprosthesis comprising a tubular scaffold implanted within a bodily lumen, wherein a substrate of the endoprosthesis has been modified below an abluminal surface of the scaffold by a laser to have gas-filled voids embedded within the substrate below the abluminal surface, the voids sized to increase scattering of optical radiation from within the substrate, the method comprising:
   passing optical radiation across an external surface of the substrate of the endoprosthesis; and
   obtaining an image by optical coherence tomography (OCT) processing of light that has been scattered by the gas-filled voids from within the substrate below the abluminal surface modified by the laser, the obtained image includes an image signal corresponding to an interior substrate portion having the voids, wherein the image signal differentiates the interior substrate portion having the gas-filled voids from empty space outside of the substrate.

2. The method of claim 1, further comprising inserting a catheter through the endoprosthesis, and emitting optical radiation from the catheter, and using the catheter to sense the light that has been scattered from within the substrate.

3. The method of claim 1, wherein the optical radiation that is passed across the external surface of the substrate is infrared light.

4. The method of claim 1 wherein, in the obtained image, the image signal that differentiates the interior substrate portion has an intensity that is greater than would be obtained from another interior substrate portion that is not modified to have the voids.

5. The method of claim 1 wherein, in the obtained image, the image signal that differentiates the interior substrate portion has an intensity that is greater than another interior substrate portion of the substrate that is closer to either an abluminal surface or a luminal surface of the substrate.

6. The method of claim 1 wherein, in the obtained image, the image signal that differentiates the interior substrate portion has an intensity that is greater in a first longitudinal segment of the endoprosthesis as compared to a second longitudinal segment of the endoprosthesis.

7. The method of claim 1, further comprising:
   prior to the passing of optical radiation, modifying the substrate of the endoprosthesis with the laser to form the voids embedded within the substrate, the voids sized to scatter optical radiation from within the substrate so as to allow production of the optical coherence tomography (OCT) image that distinguishes the interior region of the substrate from the empty space outside of the substrate.

8. The method of claim 7, wherein prior to the obtaining of the image, the substrate has been cut to form a plurality of radially deformable rings, wherein the modifying of the substrate is performed before the cutting.

9. The method of claim 8, wherein at least one of the rings is modified to have the voids, and at least another one of the rings is not modified to have the voids.

10. The method of claim 7, wherein prior to the obtaining of the image, the substrate has been cut to form a plurality of radially deformable rings, wherein the modifying of the substrate is performed after the cutting.

11. The method of claim 7, further comprising, prior to the passing of optical radiation, crimping the endoprosthesis onto a catheter, wherein the modifying of the substrate is performed before the crimping.

12. The method of claim 7, further comprising, prior to the passing of optical radiation, crimping the endoprosthesis onto a catheter, wherein the modifying of the substrate is performed after the crimping.

13. The method of claim 7, wherein modifying the substrate includes forming a greater number of the voids at a first region within the substrate that is adjacent to a first external surface of the substrate as compared to a second region within the substrate that is adjacent to a second external surface of the substrate, and the first and second external surfaces face outward in opposite directions.

14. The method of claim 7, wherein modifying the substrate includes forming the voids such that the voids are distributed entirely across a width of the substrate, and the width is a total distance between opposite side surfaces that connect abluminal and luminal surfaces of the substrate.

15. The method of claim 7, wherein the abluminal surface of the substrate above the voids that are formed is undamaged when the laser modifies the substrate.

* * * * *